(12) United States Patent
Barreiro et al.

(10) Patent No.: US 6,666,872 B2
(45) Date of Patent: Dec. 23, 2003

(54) SINGLE SHOT MENISCAL REPAIR DEVICE

(75) Inventors: Peter Barreiro, West Haven, CT (US); Daniel R. Lee, Gainesville, FL (US); Richard M. Hammond, Northford, CT (US); Peter Miller, Largo, FL (US)

(73) Assignee: United States Surgical, Norwalk, CT (US)

( * ) Notice: Subject to any disclaimer, the term of this patent is extended or adjusted under 35 U.S.C. 154(b) by 103 days.

(21) Appl. No.: 09/829,804

(22) Filed: Apr. 10, 2001

(65) Prior Publication Data

US 2002/0002374 A1 Jan. 3, 2002

Related U.S. Application Data

(60) Provisional application No. 60/196,517, filed on Apr. 11, 2000.

(51) Int. Cl.[7] .............................................. A61B 17/04
(52) U.S. Cl. ....................................................... 606/142
(58) Field of Search .................................. 606/142, 219

(56) References Cited

U.S. PATENT DOCUMENTS

| 2,075,508 A | | 3/1937 | Davidson ..................... 128/335 |
|---|---|---|---|
| 2,199,025 A | | 4/1940 | Conn ........................... 128/335 |
| 2,802,468 A | | 8/1957 | Everett ......................... 128/339 |
| 2,968,041 A | | 1/1961 | Skold ............................ 1/49.1 |
| 3,123,077 A | | 3/1964 | Alcamo ..................... 128/335.5 |
| 3,275,212 A | | 9/1966 | Johnson |
| 3,570,497 A | | 3/1971 | Lemole ..................... 128/335.5 |
| 3,643,851 A | * | 2/1972 | Green et al. ................. 227/120 |
| 3,650,453 A | | 3/1972 | Smith, Jr. |
| 3,675,688 A | | 7/1972 | Bryan et al. |
| 3,819,100 A | | 6/1974 | Noiles et al. |
| 3,875,946 A | | 4/1975 | Duncan ....................... 128/339 |
| 3,890,975 A | | 6/1975 | McGregor ................... 128/339 |
| 3,949,924 A | | 4/1976 | Green |
| 3,955,581 A | | 5/1976 | Spasiano et al. |
| RE28,932 E | | 8/1976 | Noiles et al. |
| 3,976,079 A | | 8/1976 | Samuels et al. ............ 128/335 |
| 3,981,307 A | | 9/1976 | Borysko ...................... 128/339 |

(List continued on next page.)

FOREIGN PATENT DOCUMENTS

| EP | 314412 | 5/1989 |
|---|---|---|
| EP | 390613 | 10/1990 |
| GB | 2118474 | 11/1983 |
| WO | 8903396 | 6/1986 |
| WO | 8701270 | 3/1987 |

OTHER PUBLICATIONS

US 5,035,707, 7/1991, Korthoff (withdrawn)
Hennings "Arthroscopic Repair of Meniscus Tears" Orthopedics, vol. 6, No. 9, pp. 1130–1132 (1983).
Clancy, Jr. MD et al. "Arthroscopic Meniscal Repair" Orthopedics, vol. 6, No. 9, pp1125–1129 (1983).
Justin "A Needle Guided Resorbable Staple for Arthoscopic Meniscal Repair" pp 127–130.
DiStefano MD et al. "A Technique of Arthrosdopic Meniscoplasty" Orthropedics vol. 6, No. 9, pp. 1135–1140 (1983).

*Primary Examiner*—Gary Jackson

(57) ABSTRACT

A surgical fastener application apparatus for applying surgical fasteners of general U-shape to body tissue is provided which includes a housing having a handle portion and a trigger mechanism, an elongated body portion extending from the housing, the elongated body portion having generally annular cross-sectional area substantially along the length thereof and defining a longitudinal pathway therein, and a firing mechanism operatively connected to the housing and including a pair of substantially parallel push rods positioned within the longitudinal pathway of the elongated body portion, the firing mechanism being capable of driving a surgical fastener inserted in a distal end portion of elongated body portion to the body tissue in response to operation of the trigger mechanism.

14 Claims, 6 Drawing Sheets

U.S. PATENT DOCUMENTS

| | | |
|---|---|---|
| 4,127,227 A | 11/1978 | Green |
| 4,196,836 A | 4/1980 | Becht |
| 4,204,623 A | 5/1980 | Green |
| 4,265,226 A | 5/1981 | Cassimally ................ 128/1 R |
| 4,344,193 A | 8/1982 | Kenny ......................... 3/1.911 |
| 4,359,053 A | 11/1982 | Benjamin ................... 128/339 |
| 4,403,693 A | 9/1983 | Froehlich |
| 4,410,125 A | 10/1983 | Noiles et al. |
| 4,456,006 A | 6/1984 | Wevers et al. |
| 4,462,395 A | 7/1984 | Johnson ................... 128/92 B |
| 4,470,532 A | 9/1984 | Froehlich |
| 4,478,362 A | 10/1984 | Foslien |
| 4,505,273 A | 3/1985 | Braun et al. |
| 4,513,746 A | 4/1985 | Aranyi et al. |
| 4,523,695 A | 6/1985 | Braun et al. |
| 4,523,707 A | 6/1985 | Blake, III et al. |
| 4,527,726 A | 7/1985 | Assell et al. |
| 4,534,351 A | 8/1985 | Rothfuss et al. |
| 4,549,545 A | 10/1985 | Levy .......................... 128/335 |
| 4,569,469 A | 2/1986 | Mongeon et al. |
| 4,583,670 A | 4/1986 | Alvarado |
| 4,591,086 A | 5/1986 | Campbell et al. |
| 4,592,498 A | 6/1986 | Braun et al. |
| 4,596,350 A | 6/1986 | Smith et al. |
| 4,618,086 A | 10/1986 | Li et al. |
| 4,619,391 A | 10/1986 | Sharkany et al. |
| 4,635,637 A | 1/1987 | Schreiber .................... 128/337 |
| 4,649,920 A | 3/1987 | Rhum ..................... 128/335.5 |
| 4,662,555 A | 5/1987 | Thornton |
| 4,664,304 A | 5/1987 | Wendt et al. |
| 4,664,305 A | 5/1987 | Blake, III et al. ............. 227/19 |
| 4,691,853 A | 9/1987 | Storace |
| 4,696,300 A * | 9/1987 | Anderson ............... 273/DIG. 5 |
| 4,712,550 A | 12/1987 | Sinnett ................... 128/334 R |
| 4,738,255 A | 4/1988 | Goble et al. ............ 128/92 YF |
| 4,741,330 A | 5/1988 | Hayhurst ................ 128/92 YF |
| 4,781,190 A | 11/1988 | Lee ........................ 128/334 R |
| 4,790,303 A | 12/1988 | Steffee .................. 128/924 M |
| 4,796,793 A | 1/1989 | Smith et al. |
| 4,807,628 A | 2/1989 | Peters et al. |
| 4,813,586 A | 3/1989 | Seifert |
| 4,841,960 A | 6/1989 | Garner .................... 128/92 YF |
| 4,858,603 A | 8/1989 | Clemow et al. ........ 128/92 ZW |
| 4,869,242 A | 9/1989 | Galluzzo ............... 128/92 ZW |
| 4,873,976 A | 10/1989 | Schreiber ................ 128/334 R |
| 4,875,479 A | 10/1989 | Belykh et al. ........... 128/335.5 |
| 4,887,756 A | 12/1989 | Puchy |
| 4,895,148 A | 1/1990 | Bays et al. .................. 606/213 |
| 4,901,712 A | 2/1990 | Voegell et al. ................ 606/75 |
| 4,924,865 A | 5/1990 | Bays et al. .................... 606/77 |
| 4,926,860 A | 5/1990 | Stice et al. ................. 606/144 |
| 4,950,285 A | 8/1990 | Wilk ........................... 606/232 |
| 4,951,860 A | 8/1990 | Peters et al. |
| 4,976,686 A | 12/1990 | Ball et al. |
| 4,976,715 A | 12/1990 | Bays et al. .................... 606/77 |
| 4,981,149 A | 1/1991 | Yoon et al. ................. 128/898 |
| 4,994,065 A | 2/1991 | Gibbs et al. .................. 606/92 |
| 4,994,073 A | 2/1991 | Green |
| 4,997,436 A | 3/1991 | Oberlander ................. 606/142 |
| 5,002,562 A | 3/1991 | Oberlander ................. 606/221 |
| 5,037,422 A | 8/1991 | Hayhurst et al. |
| 5,053,047 A | 10/1991 | Yoon .......................... 606/223 |
| 5,059,206 A | 10/1991 | Winters ...................... 606/213 |
| 5,100,417 A | 3/1992 | Cerier et al. |
| 5,102,421 A | 4/1992 | Anspach, Jr. ............... 606/232 |
| 5,114,065 A | 5/1992 | Storace |
| 5,141,520 A | 8/1992 | Goble et al. |
| 5,152,765 A | 10/1992 | Ross et al. |
| 5,154,189 A | 10/1992 | Oberlander ................. 128/898 |
| 5,161,725 A | 11/1992 | Murray et al. |
| 5,192,288 A | 3/1993 | Thompson et al. |
| 5,203,784 A | 4/1993 | Ross et al. |
| 5,220,928 A | 6/1993 | Oddsen et al. |
| 5,224,946 A | 7/1993 | Hayhurst et al. |
| 5,236,431 A | 8/1993 | Gogolewski et al. |
| 5,257,713 A | 11/1993 | Green et al. |
| 5,258,010 A | 11/1993 | Green et al. |
| 5,258,016 A | 11/1993 | DiPoto et al. |
| 5,261,914 A | 11/1993 | Warren |
| 5,269,783 A | 12/1993 | Sander ......................... 606/72 |
| 5,285,010 A | 2/1994 | Huber |
| 5,328,077 A | 7/1994 | Lou |
| 5,364,400 A | 11/1994 | Rego, Jr. et al. |
| 5,370,662 A | 12/1994 | Stone et al. |
| 5,374,268 A | 12/1994 | Sander |
| 5,423,471 A | 6/1995 | Mastri et al. |
| 5,643,319 A | 7/1997 | Green et al. ................. 606/218 |
| 5,702,462 A | 12/1997 | Oberlander ................. 128/898 |
| 6,190,401 B1 | 2/2001 | Green et al. ................. 606/224 |
| 6,387,113 B1 * | 5/2002 | Hawkins et al. ......... 227/180.1 |

* cited by examiner

SINGLE SHOT MENISCAL REPAIR DEVICE

This application claims the benefit of Provisional application Ser. No. 60/196,517, filed Apr. 11, 2000.

BACKGROUND

1. Technical Field

The present disclosure relates generally to the field of endoscopic surgical devices. More specifically, the present disclosure relates to an endoscopic fastener applying device for repairing torn tissue such as torn meniscus tissue.

2. Background of Related Art

One known technique for repairing torn meniscus tissue involves the use of a pair of surgical needles which are inserted through cannuli into the knee on opposite sides of a meniscal tear. The ends of the needles include a length of suture material which is pushed down through the cannuli and across the tear. An incision is made in the skin at the point where the needle exits the knee joint so that the leading end of each needle may be grasped and pulled through the joint. The ends of the sutures are then grasped after the needles are removed from the suture ends and the suture is then tied so that a horizontal suture is created in the meniscus. This procedure is repeated for placement of as many sutures as necessary to repair the meniscus tear. As is apparent, this process is both time consuming and difficult to effect.

A subsequent improvement over this procedure is outlined in U.S. Pat. No. 5,002,562, the contents of which are incorporated herein by reference. In this procedure, a barbed clip and an instrument for applying the clip are utilized. The instrument has a pair of opposed arcuate jaws which are shaped to hold a complementary-shaped curved surgical clip therebetween, such that the barbs of the clip are retained within notches in the jaws until the clip is inserted. The legs of the clip are joined by a flexible suture material. The jaws are biased in a normally open position, and as the jaws are pushed into the tissue, the jaws are scissored or closed together until they preferably overlap to move the legs of the clip together until they cross. The jaws are then reopened and backed out of the tissue, with the barbs of the clip retaining the clip in position in the tissue.

A further refinement to meniscal repair is illustrated in U.S. Pat. No. 5,997,552, the contents of which are incorporated herein by reference. This patent details a meniscal fastener applying device which applies fasteners sequentially from a longitudinally extending magazine. An advancing mechanism is operatively associated with an elongated body portion of the device for sequentially advancing surgical fasteners from a fastener supply to a firing position in alignment with a firing mechanism. The fastener includes a pair of anchor members whose proximal-most ends are connected by a suture material offset from the central longitudinal axis thereof. Because of the parallel over-under orientation of the firing mechanism and the longitudinally extending fastener magazine, the elongated body portion of the device requires a substantial cross-sectional area and necessarily requires a correspondingly wide distension of the knee joint to access the meniscal tissue to be repaired.

SUMMARY

A single shot meniscal repair device is provided which incorporates a minimally sized elongate body portion configured to hold a single fastener adjacent a distal end thereof. The elongate body portion is part of a disposable loading unit structure which facilitates up to 360° rotation about the longitudinal axis of the elongate body portion. In an alternate embodiment, at least a distal portion of the elongate body portion is angled off axis to enhance the versatility of the device. The fastener applied by the device includes a pair of anchor members interconnected by a flexible material. The flexible material extends from a respective side of the anchor members, thus maintaining the proximal ends thereof clear to receive the full driving force from the firing assembly without the risk of damaging the connecting flexible material.

BRIEF DESCRIPTION OF THE DRAWINGS

Various embodiments are described herein with reference to the drawings, wherein.

DETAILED DESCRIPTION OF PREFERRED EMBODIMENTS

Figure 1:
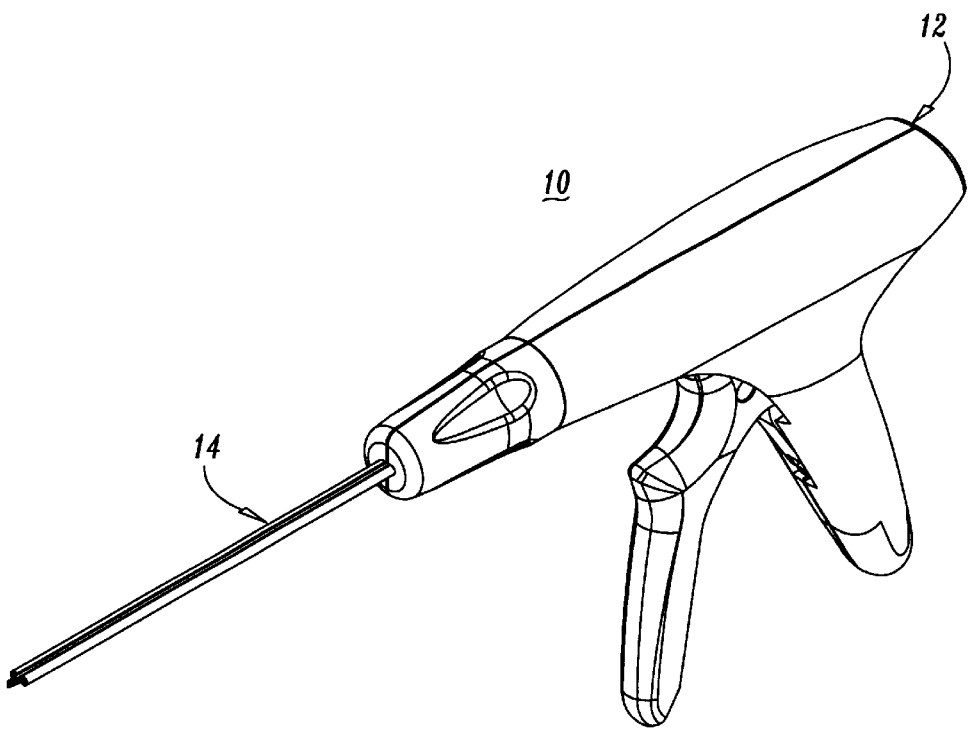
FIG. 1 is a perspective view of one embodiment of the meniscal repair device of the present disclosure.

Preferred embodiments of the presently disclosed stapler will now be described in detail with reference to the drawings, in which like reference numerals designate identical or corresponding elements in each of the several views.

Referring now to the drawings, FIG. 1 illustrates a first embodiment of the fastener applying device shown generally as 10. Briefly, the staple applying device 10 includes a housing assembly 12 and a disposable loading unit 13 having an elongated body portion 14 defining a longitudinal axis thereof. The elongated body portion 14 is preferably minimally dimensioned for arthroscopic utilization.

Figure 2:
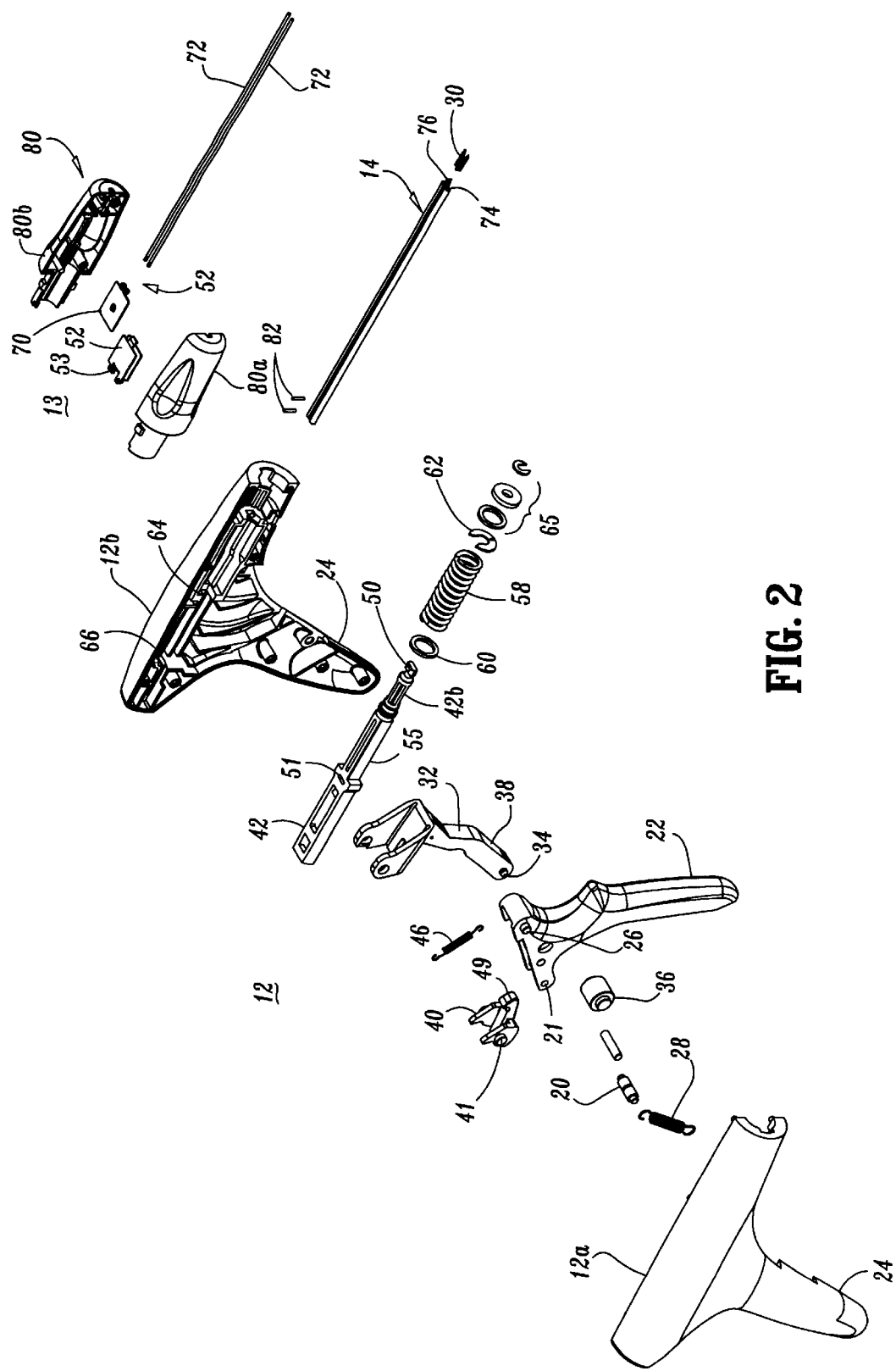
FIG. 2 is a perspective view with parts separated of the meniscal repair device of FIG. 1.

The components of the housing assembly 12 of the fastener applying device 10 are best illustrated in FIG. 2. The housing assembly 12 includes a housing formed from molded housing half-sections 12a and 12b within which the components of the housing assembly 12 are positioned. The housing assembly 12 further includes a movable handle 22 and a stationary handle 24 which is formed from portions extending from housing half-sections 12a and 12b to form a pistol grip type handle. Movable handle 22 and stationary handle 24 facilitate remote actuation of a firing assembly 52 through the elongated body portion 14 to effect the ejection of a surgical fastener 30 from the distal end of the elongated body portion 14.

The movable handle member 22 is secured to the housing half sections 12a and 12b by a pin 26 which permits rotation of the movable handle 22 relative to the stationary handle 24. A handle spring 28 is connected to the movable handle 22 by a pin 20 and to the housing 12 by a pin 34 so as to bias the movable handle 22 to an open position. The pin 20 is dimensioned to be received in openings 21 formed in the movable handle 22.

An actuation arm member 32 is operatively associated with the movable handle 22 and is pivotably connected to the lower end of the stationary handle 24 by pin 34. A cam roller member 36 is rotatably mounted to the movable handle 22 and is configured to engage and move along a cam path surface 38 defined on the actuation arm member 32 by the proximal facing outer surface thereof. Engagement between the cam roller member 36 and the cam path surface 38 effectuates counter-clockwise rotation of the actuation arm member 32 about pin 34 when the instrument is viewed from the right side, as shown in FIG. 2.

A latch member 40 is pivotably mounted to the top portion of the actuation arm 32 by pivot members 41. The latch member 40 is dimensioned and configured to detachably engage with a firing block 42 which is slidably mounted in the housing assembly 12. An engaging spring 46 connects the latch member 40 to the actuation arm member 32 so as to pivot the latch member 40 about pivot members 41 into engagement with the firing block 42. The latch member 40 has a hook member 49 pivotable about pivot members 41 into engagement with a post 51 formed on the firing block 42.

As mentioned above, the firing block 42 is slidably mounted in the housing assembly 12 and is movable in response to corresponding movement of the movable handle member 22. A mounting projection 50 extends from the end of the firing block 42 and is dimensioned and configured so as to detachably engage with the proximal end 53 of firing plate 52.

A bearing washer 60 is received about and engages a central portion 55 of the firing block 42, and a snap washer 62 is fixedly attached to the distal end portion 42b of the firing block 42 to capture and retain a compression spring 58 therebetween. Upon actuation of the handle assembly, the compression spring 58 is compressed between bearing washer 60 and snap washer 62 creating a force urging firing block 42 in a distal direction. Additional washers 65 for sealing, spacing and fitting purposes may be operatively associated with the distal end portion 42b of the firing block 42.

As described above, proximal movement of the movable handle 22 causes the cam roller 36 to engage the cam path surface 38 and rotate actuating arm member 32 and latch member 40 in a counter-clockwise direction when viewing the instrument from the right side, as shown in FIG. 2. The hook member 49 formed on the latch member 40 engages post 51 formed on the firing block 42 to slide the firing block 42 proximally as latch member 40 and actuating cam member 32 rotate counter-clockwise in response to proximal movement of handle 22. The proximal movement of the firing block 42 causes bearing washer 60 to engage a bearing surface 64 defined on the interior of the housing assembly 12 (See FIG. 2). As the firing block 42 is moved proximally, the compression spring 58 is compressed between the washer 60 and the snap washer 62 creating a force urging firing block 42 in a distal direction. After the spring 58 has been compressed, the latch member 40 contacts a camming wall 66 defined in the proximal end portion of the housing assembly 12 which, in turn, causes the latch member 40 to pivot clockwise about members 41 to disengage hook member 49 from post 51. The release of stored energy from the compression spring 58 urges the firing block 42 to move distally resulting in corresponding distal movement of the firing plate 52.

As firing plate 52 moves distally, it engages rod holder 70 and continues in combined distal movement to drive parallel push rods 72 distally to engage and eject fastener 30. Upon completion of the firing motion, handle 22 is relaxed thus withdrawing firing block 42 and firing plate 52 proximally relative to rod holder 70 and push rods 72.

The disposable loading unit 13 includes rotational housing 80 formed of housing half-sections 80a and 80b. Mounted within housing 80 are the firing plate 52 and rod holder 70. The elongate body portion 14 is mounted to housing 80 by pins 82 and extends distally therefrom. Push rods 72 are attached to rod holder 70 and are disposed within the elongate body portion 14. A new fastener 30 is disposed adjacent a distal end 74 of elongate body portion 14.

Once firing is completed, the expended disposable loading unit 13 is rotated relative to the housing 12 effectively disengaging firing plate 52 from mounting projection 50 on firing block 42. The expended disposable loading unit is then withdrawn distally from housing 12 and discarded. A new disposable loading unit is inserted into housing 12 and rotated to engage mounting projection 50 with proximal end 53 of mounting plate 52. The device 10 is then ready for subsequent firing.

Figure 3:
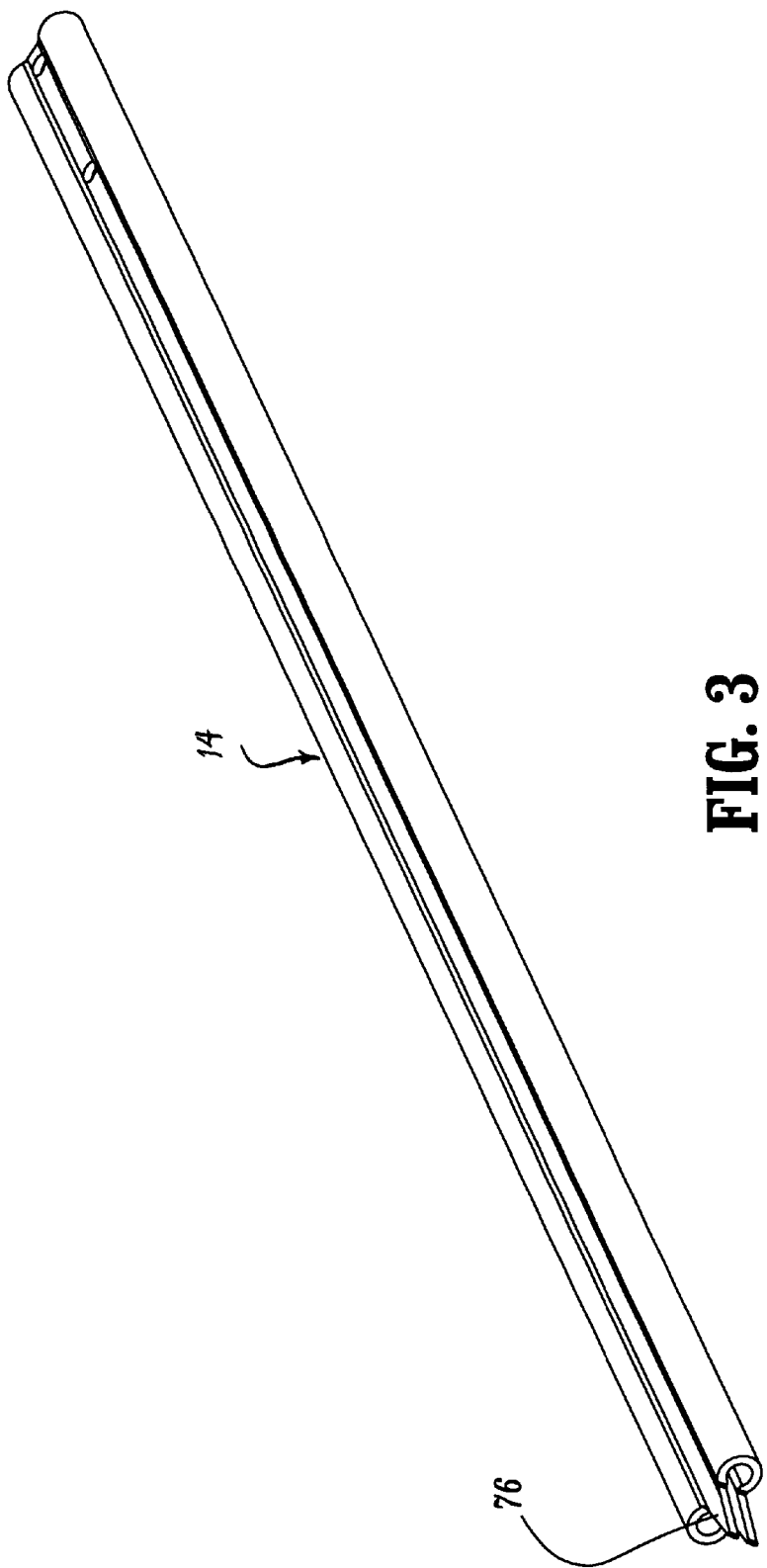
FIG. 3 is a perspective view showing the elongate body portion of the meniscal repair device of FIG. 1.

Referring to FIG. 3, the elongate body portion 14 is illustrated in a series of views. Rods 72 are configured and dimensioned to travel coaxially within the elongate body portion 14. The cross-sectional dimensions of elongate body portion 14 are minimized to more easily facilitate introduction to the operative site. A locating barb 76 can be positioned at a distal end of the elongate body portion 14 to assist in stabilizing the device at the firing point.

Figure 4:
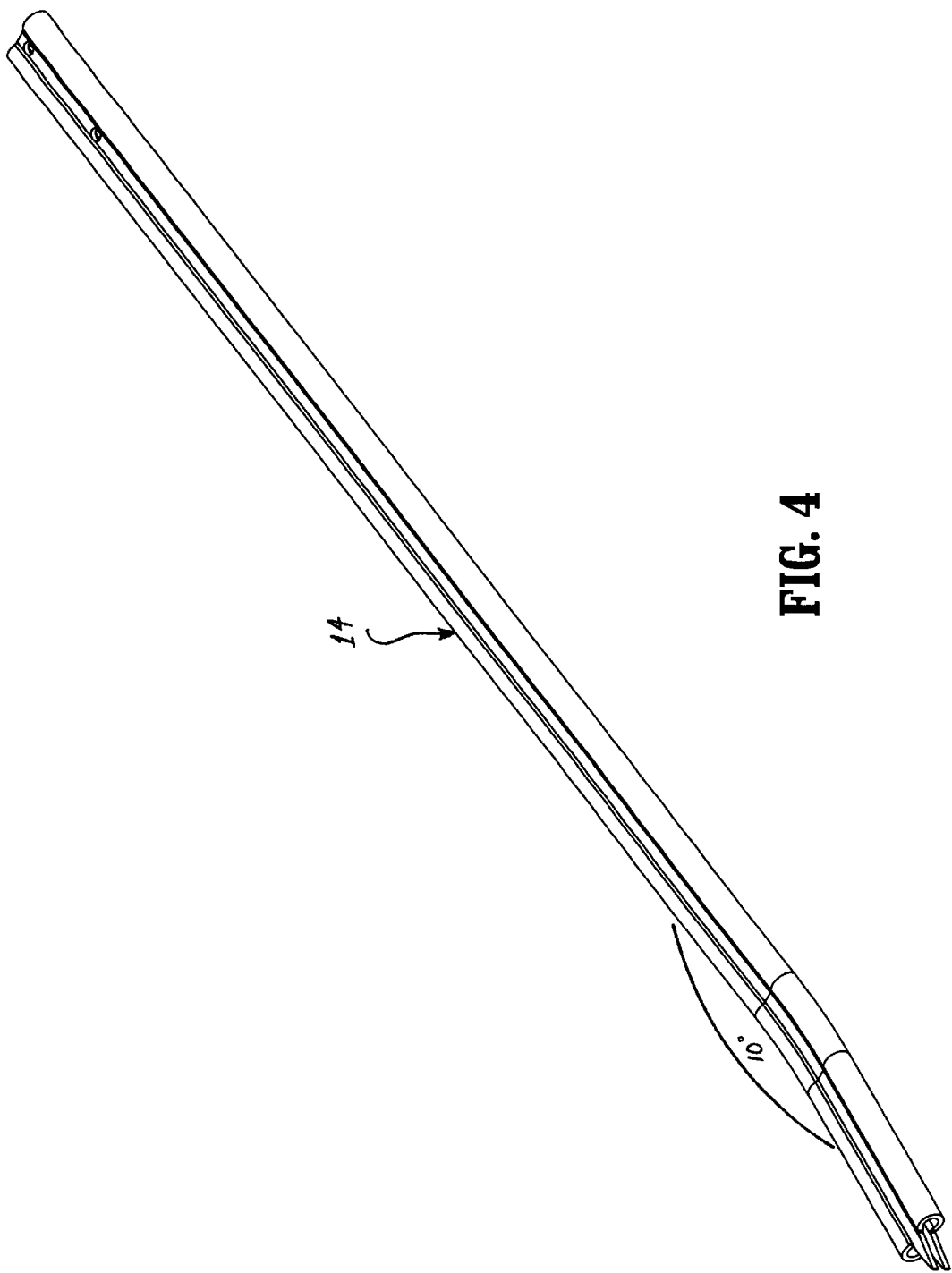
FIG. 4 is a perspective view showing a 10° upsweep version of the elongate body portion in accordance with one embodiment of the meniscal repair device of the present disclosure.
Figure 5:
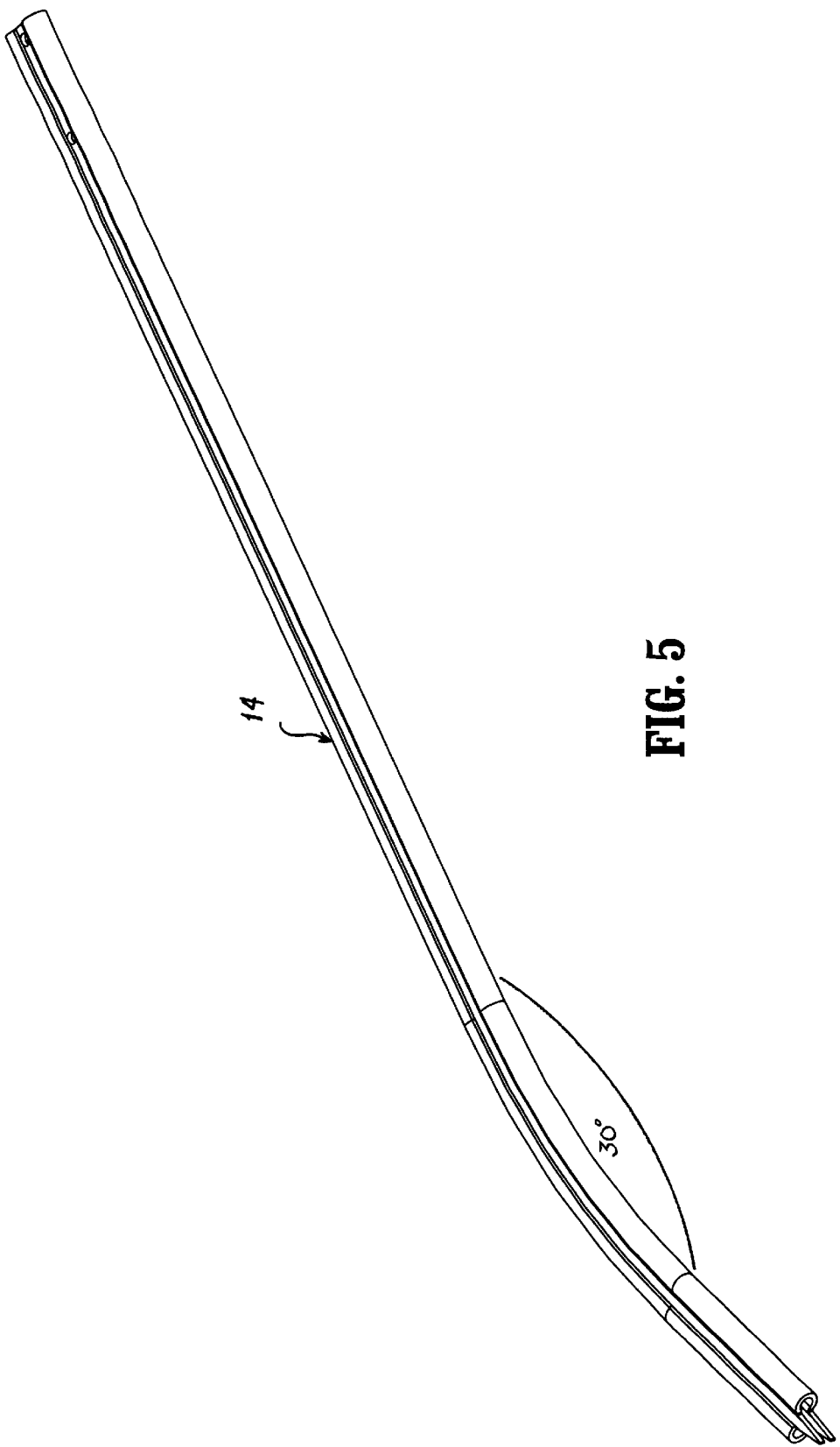
FIG. 5 is a perspective view showing a 30° left/right bend version of the elongate body portion in accordance with one embodiment of the meniscal repair device of the present disclosure.

FIGS. 4 and 5 illustrate alternate embodiments of elongate body portion 14 wherein the distal portion is upswept by 10° (FIG. 4) or bent left/right by 30° (FIG. 5). Elongate body portions shown in FIGS. 4 and 5 are otherwise substantially the same as shown in FIG. 3.

Figure 6:
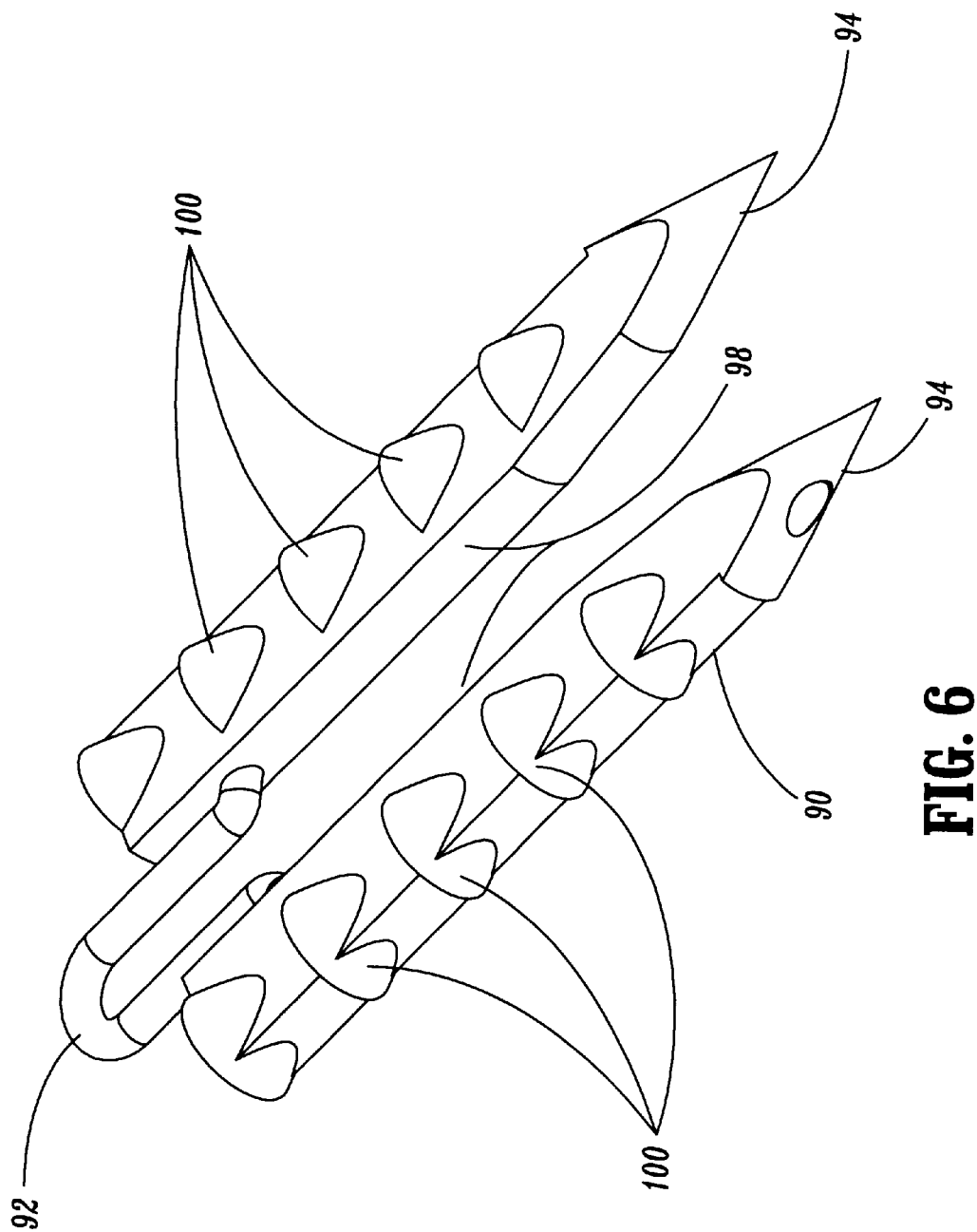
FIG. 6 is an enlarged perspective view showing the fastener used in the meniscal repair device of the present disclosure.

A fastener 30 for use in device 10 is illustrated in FIG. 6 in a series of views. Fastener 30 includes a pair of anchor members 90 linked by a flexible member 92. Preferably, the entire fastener is formed of bioabsorbable material which resorbs at an appropriate rate to facilitate healing of a tear in the meniscus. Each of the anchors 90 has a tapered distal end 94 and a planar proximal end 96. Flexible member 92 extends between adjacent side surfaces 98 of anchors 90 spaced between the proximal end 96 and the distal end 94 thereof. This configuration protects the flexible member 92 from inadvertent damage caused by the rods 72. Each anchor member 90 is further provided with a series of radial projections 100 on its periphery to inhibit withdrawal of the anchor members 90 once they have been positioned within body tissue.

What is claimed is:

1. A surgical fastener application apparatus for applying surgical fasteners of general U-shape to body tissue, comprising:

a housing including a handle portion and a trigger mechanism;

an elongated body portion extending from the housing and defining a longitudinal axis, the elongated body portion having a generally annular cross-sectional area substantially along the length thereof and defining a longitudinal pathway therein;

a firing mechanism operatively connected to the housing and including a pair of substantially parallel push rods positioned within the longitudinal pathway of the elongated body portion, the firing mechanism being capable of driving a surgical fastener inserted in a distal end portion of the elongated body portion to the body tissue in response to operation of the trigger mechanism; and a manually operable member operatively connected to the elongated body portion and engageable by a user, the manually operable member adapted for movement relative to the housing to cause corresponding rotational movement of the elongated body portion about the longitudinal axis.

2. The surgical fastener application apparatus of claim 1 wherein the pair of push rods of the firing mechanism is adapted to engage proximal end portions of the surgical fastener thereby to drive the surgical fastener to the body tissue.

3. The surgical fastener application apparatus of claim 1 wherein the firing mechanism further includes a firing plate for driving of the surgical fastener.

4. The surgical fastener application apparatus of claim 3 wherein the firing mechanism further includes a rod holder engaged with the firing plate and adapted to hold the pair of push rods.

5. The surgical fastener application apparatus of claim 1 wherein the longitudinal pathway of the elongated body portion is configured to isolate each of said push rods from one another.

6. The surgical fastener application apparatus of claim 1 wherein a distal portion of the elongated body portion is angled a predetermined degree relative to a proximal portion thereof.

7. The surgical fastener application apparatus of claim 1 wherein the elongated body portion including a locating barb disposed adjacent a distal end portion of the elongated body portion to assist in stabilizing the apparatus at a firing point in the body tissue.

8. A surgical apparatus, which comprises:

a housing dimensioned for engagement by the hand of a user;

an elongated body portion extending from the housing, the elongated body portion defining a central longitudinal axis and having proximal and distal ends;

a single fastener mounted adjacent the distal end of the elongated body portion, the fastener having a pair of anchor legs interconnected by a flexible member;

at least one push rod disposed within the elongated body portion, the one push rod adapted for longitudinal movement to deploy the fastener into tissue; and a trigger mounted to the housing and operatively connected to the one push rod, the trigger movable relative to the housing to cause corresponding movement of the one push rod, the trigger being operatively engageable with a resilient spring disposed within the housing wherein movement of the trigger a first distance at least partially compresses the spring and movement of the trigger a second distance causes release of the resilient spring and consequent return of the resilient spring to an uncompressed condition, to thereby operatively engage the one push rod and effect longitudinal movement thereof and deployment of the fastener into the tissue.

9. The surgical apparatus according to claim 8 including a pair of push rods disposed within the elongated body portion, the push rods adapted to engage respective anchor legs of the fastener to drive the anchor legs into tissue.

10. The surgical apparatus according to claim 8 including a rotatable member mounted to the housing and operatively engageable with the elongated body portion, the rotatable member adapted for rotational movement to selectively position the elongated body portion at predetermined angular orientations relative to the central longitudinal axis.

11. A surgical apparatus, which comprises:

a housing dimensioned for engagement by the hand of a user;

an elongated body portion extending from the housing, the elongated body portion defining a central longitudinal axis and having proximal and distal ends, the elongated body portion having an offset portion adjacent the distal end thereof, the offset portion being arranged in oblique relation relative to the longitudinal axis;

a single fastener mounted adjacent the distal end of the elongated body portion, the fastener having a pair of anchor legs interconnected by a flexible member;

at least one push rod disposed within the elongated body portion, the one push rod adapted for longitudinal movement to deploy the fastener into tissue; and a trigger mounted to the housing and operatively connected to the one push rod, the trigger movable relative to the housing to cause corresponding movement of the one push rod.

12. A method for repair of a tear in a meniscus, comprising the steps of:

accessing a meniscus of a patient;

positioning a surgical instrument adjacent the meniscus, the surgical instrument including an elongated body portion and having a single meniscal fastener mounted to the elongated body portion, the elongated body portion having a positioning barb, the meniscal fastener including a pair of anchor legs and a flexible member interconnecting the anchor legs;

orienting the surgical instrument relative to the meniscus such that the anchor legs are disposed in opposite sides of a tear in the meniscus and advancing the positioning barb into tissue adjacent the tear;

actuating the surgical instrument to deploy the single meniscal fastener whereby the anchor legs penetrate the meniscus and the flexible member at least partially spans the tear therein.

13. The method according to claim 12 wherein the step of orienting includes rotating the elongated body portion with a manually manipulative member to arrange the elongated body portion at a predetermined angle of orientation.

14. The surgical apparatus, which comprises:

a housing dimensioned for engagement by the hand of a user;

an elongated body portion extending from the housing, the elongated body portion defining a central longitudinal axis and having proximal and distal ends, the elongated body portion having a penetrating member in general parallel relation to the central longitudinal axis, the penetrating member adapted to penetrate tissue to facilitate positioning of the elongated body portion relative to the tissue;

a single fastener mounted adjacent the distal end of the elongated body portion, the fastener having a pair of anchor legs interconnected by a flexible member;

at least one push rod disposed within the elongated body portion, the one push rod adapted for longitudinal movement to deploy the fastener into tissue; and a trigger mounted to the housing and operatively connected to the one push rod, the trigger movable relative to the housing to cause corresponding movement of the one push rod.

* * * * *